(12) United States Patent
Novak et al.

(10) Patent No.: US 7,256,771 B2
(45) Date of Patent: Aug. 14, 2007

(54) APPARATUS FOR OPERATING A MEDICAL APPLIANCE

(75) Inventors: Pavel Novak, Stetten (CH); Tasso Ströhle, Messkirch (DE)

(73) Assignee: Storz Endoskop Produktions GmbH (DE)

( * ) Notice: Subject to any disclaimer, the term of this patent is extended or adjusted under 35 U.S.C. 154(b) by 342 days.

(21) Appl. No.: 10/785,696

(22) Filed: Feb. 24, 2004

(65) Prior Publication Data

US 2004/0227737 A1 Nov. 18, 2004

Related U.S. Application Data

(63) Continuation of application No. PCT/EP02/08900, filed on Aug. 9, 2002.

(30) Foreign Application Priority Data

Aug. 24, 2001 (DE) ................ 101 42 738

(51) Int. Cl.
*G09G 5/00* (2006.01)
(52) U.S. Cl. .................. 345/173; 715/773
(58) Field of Classification Search ........ 345/173–178; 715/773
See application file for complete search history.

(56) References Cited

U.S. PATENT DOCUMENTS

| | | | |
|---|---|---|---|
| 4,651,365 A | 3/1987 | Zeigler | 5/74 R |
| 4,914,624 A | 4/1990 | Dunthorn | 364/900 |
| 5,159,159 A * | 10/1992 | Asher | 178/18.05 |
| 5,705,906 A * | 1/1998 | Tanabe et al. | 318/568.13 |
| 5,890,178 A | 3/1999 | Haneda | 707/516 |
| 6,131,868 A | 10/2000 | Welling et al. | 248/276.1 |

FOREIGN PATENT DOCUMENTS

| | | |
|---|---|---|
| DE | 88 04 417 | 5/1988 |
| DE | 39 23 024 A1 | 2/1990 |
| DE | 197 14 984 C2 | 11/1999 |
| DE | 198 57 613 A1 | 6/2000 |
| DE | 199 29 907 A1 | 12/2000 |
| DE | 199 55 116 A1 | 5/2001 |
| DE | 101 42 738 C1 | 4/2003 |
| GB | 2 269 252 A | 2/1994 |
| WO | WO94/22069 | 9/1994 |

OTHER PUBLICATIONS

C. Zindel, Medical Engineering Group, Siemens AG, Erlangen, Germany, "System Solutions for the Integration of Devices in the OR", 2000, pp. 199-205, Min Invas Ther & Allied Tehchnol 2000:9 (3/4).

* cited by examiner

*Primary Examiner*—Jimmy Nguyen
*Assistant Examiner*—Tammy Pham
(74) *Attorney, Agent, or Firm*—St. Onge Steward Johnston & Reens LLC

(57) ABSTRACT

An apparatus for operating a medical appliance, such as a moving operating table, has a touchscreen on which a user interface is displayed. The user interface has a number of first buttons. A control unit initiates first actions of the medical appliance when the first buttons are actuated by a user. Furthermore, the user interface has at least one stop area which, when actuated, stops any first action. The first buttons and the stop area are spatially distributed over the user interface such that center points between each first button and the stop area are located outside each first button.

21 Claims, 1 Drawing Sheet

APPARATUS FOR OPERATING A MEDICAL APPLIANCE

CROSS-REFERENCES TO RELATED APPLICATIONS

This application is a continuation of international patent application PCT/EP02/08900 filed on Aug. 9, 2002, published in German language and designating the U.S., which international patent application claims priority of German patent application DE 101 42 738.7 filed on Aug. 24, 2001.

BACKGROUND OF THE INVENTION

The present invention relates to an apparatus for operating a medical appliance, in particular a moving operating table. More specifically, the invention relates to an apparatus for operating a medical appliance having a touchscreen on which a user interface is displayed, wherein the user interface has a number of first buttons for initiating first actions of the medical appliance.

The use of touchscreens for operating and controlling appliances has become widespread, particularly in the medical sector. A touchscreen is a screen or, more generally, a display unit having a touch-sensitive surface. A touchscreen therefore allows the pictorial representation of (virtual) buttons, the touching of which by a user can be recognized and evaluated. A touchscreen can therefore be used to implement very flexible input devices, which can also be operated very easily and intuitively.

For many appliances, particularly in the medical sector, however, an especially reliable and secure operation is required. Thus, by way of example, it must be possible to control the movement of an electric operating table very reliably in order to put a seriously injured patient carefully into a desired position. In this context, it must be ensured that the movement of the operating table can be reliably stopped again at any time. This characteristic, which at first glance is obvious, is not readily assured with known touchscreens. This is because it cannot be ruled out that the touchscreen's button will "freeze" after it has been actuated, i.e. that a malfunction in the touchscreen will cause release of the touch-sensitive button to be no longer registered. If the button has been used to start the operating table moving in such a case, the touchscreen can no longer be used to stop the movement. For this reason, critical actions on medical appliances, i.e. actions which have to be performed with a very high degree of reliability, have not solely been controlled using touchscreens so far. In some cases, such actions have been controlled entirely without a touchscreen, or the touchscreen has been complemented by an additional "real" emergency-off switch, as in the case of the apparatus mentioned at the outset.

However, the addition of an emergency-off switch requires additional wiring and also some work on the hardware of commercially available touchscreens. This is a drawback in respect of the manufacturing costs of prior art apparatuses, and also in respect of operating convenience.

An alternative option of providing reliable and failsafe control with a touchscreen involves that the individual control operations each are executed only for a predetermined, limited period of time when the button is actuated. This ensures that, by way of example, the movement of the operating table is stopped after the predetermined period of time has elapsed, even if the button on the touchscreen freezes due to a failure which has occurred in the interim. However, such a solution adversely affects operating convenience. Furthermore, it is then very difficult to set an exact position for the operating table with high precision.

SUMMARY OF THE INVENTION

Against this background, it is an object of the present invention to specify an apparatus of the kind mentioned at the outset which allows convenient and, at the same time, safe and reliable operation of a medical appliance.

It is another object to provide an apparatus for controlling a medical appliance be means of a touchscreen even in case of an emergency stop of the medical appliance.

It is yet another object to provide an apparatus that allows to conveniently control a medical appliance from a touchscreen without the need of additional emergency-off switches.

According to one aspect of the invention, these and other objects are achieved with an apparatus of the kind mentioned at the outset, in which the user interface has at least one stop area which, when actuated, stops any first action, with the first buttons and the stop area being spatially distributed over the user interface such that center points between each first button and the stop area are located outside each first button.

According to another aspect, a center point of an assumed connecting line between the centroid of any first button and the stop area is located outside from each first button.

The new apparatus makes use of the effect that, when a plurality of points on a touchscreen are actuated simultaneously, the evaluation electronics of commercially available touchscreens evaluate the center point for said points as a virtual point of contact. This applies at least to "resistive touchscreens" that are normally used for medical applications. The center point evaluated when the touchscreen is simultaneously touched at a plurality of points is sometimes referred to as the geometric center point.

The result of the inventive distribution of the first buttons and of the stop area is that the actuation of a first button can be cancelled even if the touchscreen "freezes" due to a failure at the first button actuated. This is because the evaluation electronics identify the virtual point of contact as being that point which is located midway between the frozen first button and the later point of contact in the stop area, when the touchscreen is subsequently touched in the stop area. This means that touching the touchscreen a second time allows the point of contact recognized by the evaluation electronics to be "withdrawn" from the area of the first button. For the evaluation electronics or the downstream control unit, this is equivalent to the situation in which the first button has been released again. The control unit thus recognizes that the first button has been released no later than when the user touches the touchscreen in said stop area.

It is not critical if the touchscreen "freezes" in the stop area, since this automatically results in all critical actions being stopped. Consequently, the inventive distribution of the first buttons and of the stop area ensures that an action initiated by actuating a first button can be stopped again at any time, namely at least by actuating the stop area of the touchscreen again. The stop area thus performs the function of an emergency-off switch, which means that an additional hardware emergency-off switch can be dispensed with.

In addition, the inventive distribution of the first buttons and of the stop area has the advantage that pressing the stop area of the touchscreen always results in defined interruption of the critical action. Since all conceivable center points between the stop area and the first buttons are located outside each first button, pressing the stop area of the touchscreen does either not initiate any unwanted new action. The risk of a "ping-pong" effect, for example between various directions of movement of the operating table, is prevented thereby. Furthermore, this also ensures that a critical movement is not stopped by an abrupt counter movement, which could sometimes have even worse consequences for a patient.

The inventive arrangement of the first buttons and of the stop area provides a very inexpensive and at the same time very convenient way of reliably and safely controlling even critical actions on medical appliances. In addition, the fact that all control operations, including the emergency-stop function, are initiated via the touchscreen means that a standardized and uniform operation is ensured. This is particularly advantageous in emergency situations, because it is not necessary to look for the correct switch at unfamiliar places first.

In a refinement of the invention, the stop area includes a second button.

This measure makes the stop area visually discernable for the user of the medical appliance. For the actual stop function, this is not absolutely necessary from the technical point of view. Since the touchscreen's evaluation electronics always recognize the center point between a plurality of simultaneous points of contact as being a virtual point of contact, a first button which has frozen can, in principle, be cancelled by arbitrarily touching any other place. However, visually highlighting the stop area has the advantage that the emergency-stop function puts the medical appliance into a defined off- state, which the user expects. Unintentional abrupt counter movements are more reliably prevented thereby.

In another refinement, the apparatus's control unit initiates a first action only while the associated first button is being actuated.

The result of this measure is that an initiated action in the apparatus's normal mode is terminated immediately when the user releases the associated first button. The emergency-stop function is therefore actually required only for emergency cases in which the first button freezes. This highlights the special function of the stop area to an even greater degree, which simplifies intuitive operation of the medical appliance. In addition, the measure has the advantage that the emergency-stop function is even easier to implement technically, since pressing the stop area of the touchscreen, as described above, results in the point of contact recognized by the touchscreen being moved out of the area of the first button. Consequently, said measure in combination with the inventive distribution of the buttons automatically results in the initiated action being terminated.

In another refinement, the first actions are spatial movements of the medical appliance.

The inventive arrangement of the first buttons and of the stop area is particularly advantageous when it is desired to control spatial movements of medical appliances, such as an operating table or an instrument robot. Such actions have not been controlled using touchscreens so far due to the existing reservations, except that the touchscreens have been provided with additional hardware disconnection means. The advantages of the invention therefore apply particularly when controlling spatial movements of medical appliances.

In another refinement of the invention, the control unit contains a voice input unit for receiving and evaluating voice commands.

This measure further increases the operating convenience of the apparatus. The user of the medical appliance thus has various intuitive control options available.

In another refinement of the measure cited above, the voice input unit and the user interface are coupled to one another such that at least the stop area is active whenever a voice command is input.

This measure has the advantage that even the voice control for the medical appliance does not need to be backed up by additional hardware emergency-off switches. This is because the function of the emergency-off switch can be provided reliably and at the same time inexpensively by the stop area on the touchscreen due to the relationships described earlier.

It is particularly advantageous if the user interface with the first buttons and the stop area is activated automatically as soon as a voice command is input whose function corresponds to the pressing of a first button.

It goes without saying that the features cited above and the features which are yet to be explained below can be used not only in the respectively indicated combination but also in other combinations or on their own without departing from the scope of the present invention.

Exemplary embodiments of the invention are shown in the drawing and are explained in more detail in the description below.

BRIEF DESCRIPTION OF THE DRAWING

The single FIGURE shows a schematic illustration of an exemplary embodiment of the invention. In this case, an embodiment of the new apparatus is denoted by reference numeral 10 in its entirety.

DETAILED DESCRIPTION OF PREFERRED EMBODIMENTS

Figure 1:
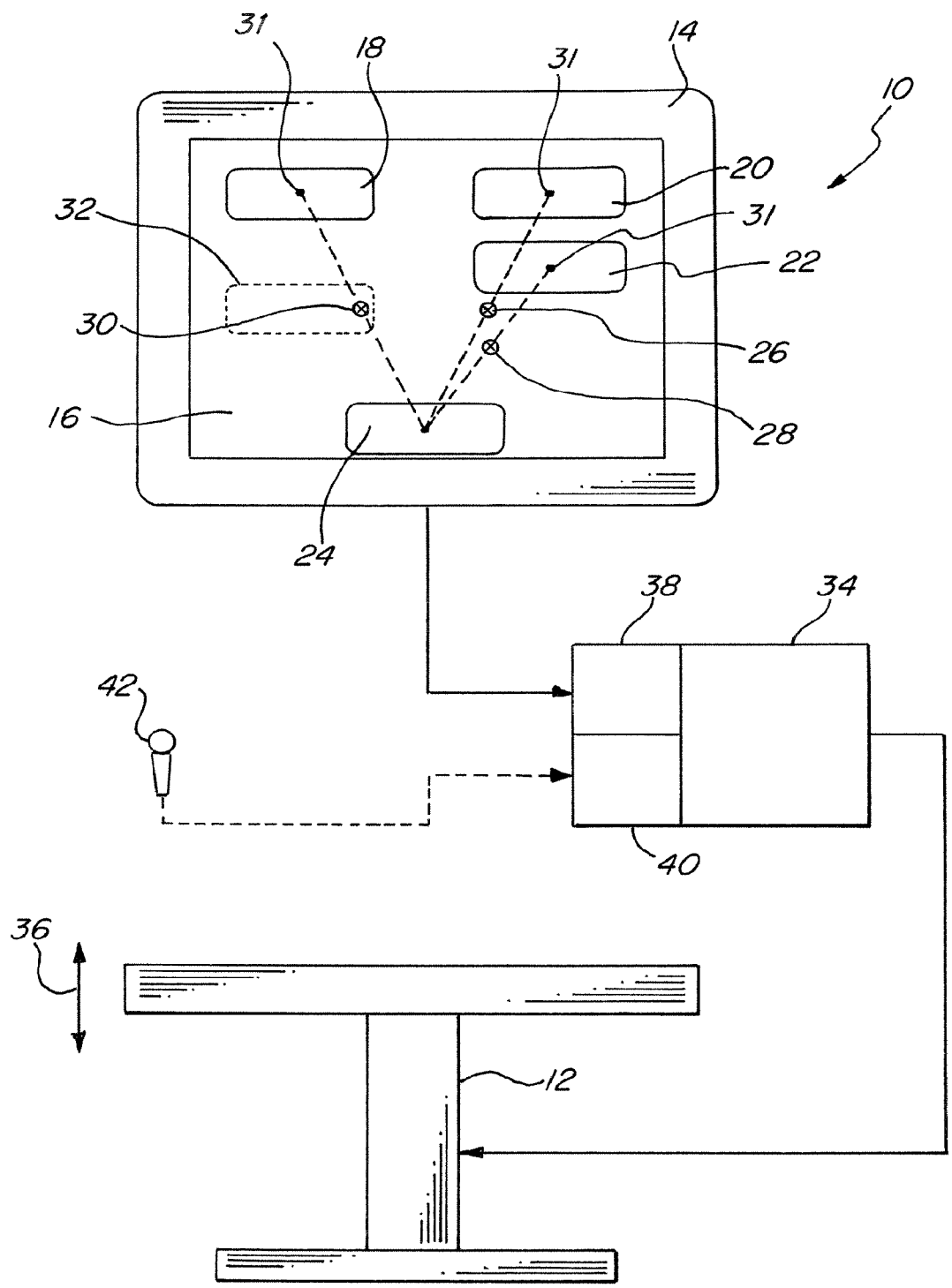

In the exemplary embodiment shown, the apparatus 10 is used for operating an electrically movable operating table 12. The invention, however, is not limited to this exemplary embodiment and it can likewise be used, by way of example, for operating a robot arm or for operating insufflators, pumps and the like.

The apparatus 10 contains a resistive touchscreen 14, known per se, on which a user interface 16 is displayed. In the schematic exemplary embodiment shown here, the user interface 16 has three first buttons 18, 20, 22. In addition, a second button 24 is shown on the user interface 16 in this case. The button 24 is entirely in a stop area which is defined by its spatial relationship with the first buttons 18 to 22, which relationship will be described in more detail below.

The reference numerals 26, 28, 30 denote the geometric center points between each first button 18, 20, 22 and the second button 24. From a pictorial point of view, the center points 26, 28, 30 are each located midway on a connecting line between the centroids 31 of the first buttons 18, 20, 22 and the second button 24.

As can be seen in the illustration, the center points 26, 28, 30 are located outside each first button 18, 20, 22. To illustrate this characteristic, the reference numeral 32 denotes the position of an assumed first button (actually not present) which would conflict with the inventive distribution. This is because arranging a button at the position 32 would result in the pressing of the second button 24 (emergency-off switch) initiating an unwanted action if the button 18 were to "freeze" on account of a failure in the touchscreen 14. Since, by contrast, center points 26, 28 are situated in an entirely neutral area of the user interface 16, pressing the second button 24 in combination with a frozen first button 20 or 22 would not result in any unwanted action. Just the action linked to the frozen button 20, 22 would be stopped.

The reference numeral 34 schematically denotes a control unit which can move the operating table 12 downwards or upwards in the direction of arrow 36. Such control units are known per se in apparatuses of the generic type, so that a more detailed description can be dispensed with here.

Reference numeral 38 schematically denotes the evaluation electronics for the touchscreen 14. For the sake of simplicity, the evaluation electronics 38 are shown in the area of the control unit 34 in this case. In practice, however, the evaluation electronics 38 are often incorporated in the housing of the touchscreen 14. In a manner which is known per se, the evaluation electronics 38 evaluate a touch in the area of the user interface 16 of the touchscreen 14 and supply the control unit 34 with data values corresponding to the recognized positions of contact. The control unit processes the data values received and controls the operating table 12 on the basis thereof.

Reference numeral 40 denotes a voice input unit which is associated with the control unit 34, again for the sake of simplicity. Alternatively, the voice input unit 14 can also be arranged separately from the control unit 34 and can be connected to it by means of a cable, for example. The voice input unit 40 receives its voice signals via a microphone 42 in a manner which is known per se. In the exemplary embodiment illustrated here, the voice control for the operating table 12 is an optional, additional variant. For this reason, the link between the microphone 42 and the control unit 34 is shown in dashes only.

According to a preferred exemplary embodiment of the invention, the control unit 34 is a commercially available computer, known per se, which has been programmed with special control software for performing the necessary control functions. In this case, the software includes an apparatus-internal function test which needs to be executed first when the apparatus has been started up. This function test involves, inter alia, checking the operability of the touchscreen 14. If failures are detected at this time, operation of the apparatus 10 is restricted or is stopped entirely. Full operation of the apparatus 10 is possible only if the initial test is performed without failure.

In addition, the software for the control unit 34 involves that, after initiation of a critical action, for example the movement 36 of the operating table 12, any contact with the touchscreen 14 outside the first button, which corresponds to the initiated function, results in a stop command. Pressing the touchscreen 14 in the area of the second button 24 therefore automatically results in the movement of the operating table 12 being stopped, even if the associated first button freezes when it has been pressed. This also applies if the movement of the operating table 12 has been initiated by means of the voice control. The second button 24 thus has the function of a general emergency-stop switch. In the normal mode of the apparatus 10, however, the movement of the operating table 12 is actually terminated when the associated first button, having been pressed, is released.

What is claimed is:

1. An apparatus for operating a medical appliance, said apparatus having: a touchscreen adapted to display a user interface, said user interface comprising a plurality of first buttons to be actuated by a user, and comprising at least one stop area, with each first button having a centroid, and a control unit connected with the touchscreen, wherein the control unit is adapted to initiate a first action of the medical appliance when a first button is actuated by a user, wherein the control unit is adapted to stop the first action, when the stop area is actuated, and wherein the plurality of first buttons and the stop area are spatially distributed over the user interface such that any center point defined on an assumed connecting line between each centroid and the stop area is located outside of each first button.

2. The apparatus according to claim 1, wherein the stop area includes a second button.

3. The apparatus according to claim 1, wherein the control unit is adapted to initiate a first action only while the associated first button is being actuated.

4. The apparatus according to claim 1, wherein the first actions are spatial movements of the medical appliance.

5. The apparatus according to claim 1, wherein the control unit includes a voice input unit for receiving and evaluating voice commands.

6. The apparatus according to claim 5, wherein the voice input unit and the user interface are coupled to one another such that at least the stop area is active whenever a voice command is input.

7. The apparatus according to claim 1, wherein the medical appliance is a moving operating table.

8. An apparatus for operating a medical appliance, said apparatus having a touchscreen adapted to display a user interface and having a control unit, wherein the user interface comprises a number of first buttons, and wherein the control unit is adapted to initiate first actions of the medical appliance when the first buttons are actuated, wherein the user interface comprises at least one stop area which, when actuated, stops any first action, and wherein the first buttons and the stop area are spatially distributed over the user interface such that center points between each first button and the stop area are located outside each first button.

9. The apparatus according to claim 8, wherein the stop area includes a second button.

10. The apparatus according to claim 8, wherein the control unit is adapted to initiate a first action only while the corresponding first button is being actuated.

11. The apparatus according to claim 8, wherein the first actions are spatial movements of the medical appliance.

12. The apparatus according to claim 8, wherein the control unit includes a voice input unit for receiving and evaluating voice commands.

13. The apparatus according to claim 12, wherein the voice input unit and the user interface are coupled to one another such that at least the stop area is active whenever a voice command is input.

14. The apparatus according to claim 8, wherein the medical appliance is a moving operating table.

15. An apparatus for operating a medical appliance, comprising:
   a touchscreen that displays a plurality of buttons and at least one stop area; and
   a control unit connected to the touchscreen;
   wherein said control unit initiates an action of the medical appliance when one of said buttons is touched by a user;
   wherein said control unit stops the action of the medical appliance when the stop area is touched by the user;
   wherein each of said buttons and said stop area has a centroid; and
   wherein said plurality of buttons and said stop area are spatially distributed on the touchscreen such that the center points of the connecting lines that connect the centroid of each of said buttons with the centroid of said stop area are located outside of each of said buttons.

16. The apparatus according to claim 15, wherein said stop area comprises an additional button.

17. The apparatus according to claim 15, wherein said control unit initiates the action of the medical appliance only when the corresponding button is being touched.

18. The apparatus according to claim 15, wherein the action of the medical appliance comprises spatial movements of the medical appliance.

19. The apparatus according to claim 15, wherein said control unit includes a voice input unit for receiving and evaluating voice commands.

20. The apparatus according to claim 19, wherein said voice input unit and said user interface are coupled to one another such that at least said stop area is active whenever a voice command is in put.

21. The apparatus according to claim 15, wherein the medical appliance comprises a moving operating table.

* * * * *